(12) United States Patent
Piao et al.

(10) Patent No.: US 12,203,676 B2
(45) Date of Patent: Jan. 21, 2025

(54) AIR DISINFECTOR

(71) Applicant: SOTO Air Purification Technology (Langfang) Co., Ltd., Langfang (CN)

(72) Inventors: Zhonghao Piao, Langfang (CN); Hui Li, Langfang (CN)

(73) Assignee: SOTO Air Purification Technology (Langfang) Co., Ltd., Langfang (CN)

( * ) Notice: Subject to any disclaimer, the term of this patent is extended or adjusted under 35 U.S.C. 154(b) by 0 days.

(21) Appl. No.: 18/644,093

(22) Filed: Apr. 24, 2024

(65) Prior Publication Data

US 2024/0271821 A1   Aug. 15, 2024

Related U.S. Application Data

(63) Continuation of application No. PCT/CN2023/085027, filed on Mar. 30, 2023.

(30) Foreign Application Priority Data

Dec. 30, 2022   (CN) .......................... 202211715197.8

(51) Int. Cl.
*F24F 13/12*   (2006.01)
*A61L 9/014*   (2006.01)
(Continued)

(52) U.S. Cl.
CPC .............. *F24F 13/12* (2013.01); *A61L 9/014* (2013.01); *A61L 9/205* (2013.01); *F24F 1/035* (2019.02);
(Continued)

(58) Field of Classification Search
CPC .. F24F 13/12; F24F 1/035; F24F 8/167; F24F 8/22; F24F 13/20; A61L 9/014; A61L 9/205; A61L 2209/12; A61L 2209/14; A61L 2209/22; B01D 46/0028; B01D 46/0036; B01D 46/24; B01D 53/885; B01D 2255/802; B01D 2265/023; B01D 2265/025; B01D 2265/028; B01D 2279/65

See application file for complete search history.

(56) References Cited

FOREIGN PATENT DOCUMENTS

CN   102221256 A   10/2011
CN   105546793 A   5/2016
(Continued)

OTHER PUBLICATIONS

Internation Search Report of PCT/CN2023/085027, Mailed May 10, 2023.

*Primary Examiner* — Sean E Conley
*Assistant Examiner* — Brendan A Hensel
(74) *Attorney, Agent, or Firm* — Xia Li

(57) ABSTRACT

The present disclosure relates to the technical field of air disinfectors, and provides an air disinfector. The air disinfector includes a shell, an air outlet window arranged in the shell, and an air guide cover vertically and slidably arranged in the air outlet window by means of a lifting mechanism. The air outlet window is used for being installed on the top of a disinfector main body. The lifting mechanism includes a lifting cover plate, a lifting rod fixed part, a plurality of anti-pinch springs and an anti-pinch limit switch. Through the technical scheme, the problem in the prior art that the gap between the air guide cover and the air outlet window is prone to pinch and hurt human hands is solved.

9 Claims, 17 Drawing Sheets

(51) Int. Cl.
  *A61L 9/20* (2006.01)
  *F24F 1/035* (2019.01)
  *F24F 8/167* (2021.01)
  *F24F 8/22* (2021.01)
  *F24F 13/20* (2006.01)

(52) U.S. Cl.
  CPC ................ *F24F 8/167* (2021.01); *F24F 8/22* (2021.01); *F24F 13/20* (2013.01); *A61L 2209/12* (2013.01); *A61L 2209/14* (2013.01); *A61L 2209/22* (2013.01)

(56) References Cited

FOREIGN PATENT DOCUMENTS

| | | | |
|---|---|---|---|
| CN | 106642618 A | 5/2017 | |
| CN | 206220729 U | 6/2017 | |
| CN | 207455766 U | 6/2018 | |
| CN | 209595073 A | 11/2019 | |
| CN | 110748994 A | 2/2020 | |
| CN | 211716745 U | 10/2020 | |
| CN | 112628998 A | 4/2021 | |
| CN | 215723966 A | 2/2022 | |
| CN | 115419986 A | 12/2022 | |
| DE | 2536671 A1 | 3/1976 | |
| FR | 646780 A | 11/1928 | |
| WO | WO-2018129974 A1 * | 7/2018 | ............ F24F 1/0011 |

* cited by examiner

AIR DISINFECTOR

CROSS-REFERENCE TO RELATED APPLICATIONS

This application is a continuation of International Patent Application No. PCT/CN2023/085027 with a filing date of Mar. 30, 2023, designating the United States, now pending, and further claims priority to Chinese Patent Application No. 202211715197.8 with a filing date of Dec. 30, 2022. The content of the aforementioned applications, including any intervening amendments thereto, are incorporated herein by reference.

TECHNICAL FIELD

The present disclosure relates to the technical field of air disinfectors, in particular to an air disinfector.

BACKGROUND

The air disinfector is a machine that disinfects air through the principles of filtration, purification and sterilization. In addition to bacterium, virus, mold and spore killing and other so-called sterilization and disinfection, some air disinfector can also remove organic pollution gas such as formaldehyde and phenol from indoor air, and can also kill or filter allergens such as pollen.

Generally, according to the assisted disinfection of the antibacterial net, nano-scale photocatalyst materials are cooperated with the irradiation of the purple lamp to produce positively charged "holes" and negatively charged negative oxygen ions on the surface of titanium dioxide. The "holes" are combined with water vapor in the air to produce strong alkaline "hydroxyl radicals". Formaldehyde and benzene in the air are decomposed into harmless water and carbon dioxide. The negative oxygen ions are combined with oxygen in the air to form "reactive oxygen". The cell membranes of bacteria and the proteins of oxidizing viruses can be decomposed so as to achieve the purposes of sterilization, disinfection and decomposition of harmful gases. In the prior art, air is pumped into the air disinfector and discharged after passing through the filter screen for disinfection. When air is exhausted, the air guide cover can rise. When the air disinfector is turned off, the air guide cover can descend. When the air disinfector is turned off, if someone accidentally puts his finger into the gap between the air guide cover and the air outlet window, the finger is easily hurt by pinching. Therefore, there is an urgent need for a lifting structure of the air guide cover that can prevent people from being hurt by pinching.

SUMMARY

The present disclosure provides an air disinfector. The problem in the prior art that the gap between the air guide cover and the air outlet window is prone to pinch and hurt human hands is solved.

The technical scheme of the present disclosure is as follows. An air disinfector includes a shell, an air outlet window arranged in the shell, and an air guide cover vertically and slidably arranged in the air outlet window by means of a lifting mechanism. The lifting mechanism includes a lifting cover plate, a lifting rod fixed part, a plurality of anti-pinch springs and an anti-pinch limit switch. The lifting cover plate is arranged in the air outlet window. The lifting rod fixed part is vertically and slidably arranged in the air outlet window. The number of the anti-pinch springs is multiple. Both ends of the anti-pinch spring act on the lifting rod fixed part and the air guide cover respectively. The anti-pinch limit switch is arranged on the lifting rod fixed part. The air guide cover is placed on the top of the lifting rod fixed part. The bottom of the air guide cover is provided with an anti-pinch trigger part. The anti-pinch trigger part is in contact with the anti-pinch limit switch.

A further technical scheme is as follows.

The lifting rod fixed part is provided with a top limit switch. The lifting cover plate is provided with an upper trigger part corresponding to the top limit switch. An inner wall of the air outlet window is provided with a bottom limit switch. The bottom of the lifting rod fixed part is provided with a lower trigger part corresponding to the bottom limit switch.

A further technical scheme is as follows.

The air outlet window is provided with a lifting motor. An output shaft of the lifting motor is connected with a lifting screw by means of a screw fixed part. The lifting screw is in screw-thread fit with the lifting rod fixed part. The top of the lifting screw abuts against the bottom of the lifting cover plate.

The air disinfector also includes a plurality of lifting limit rods. The lifting limit rods are arranged on the lifting cover plate. The lifting limit rods penetrate through the lifting rod fixed part.

A further technical scheme is as follows.

An accommodating slot is formed in the center of the lifting rod fixed part. A spiral sleeve is installed in the accommodating slot. The lifting screw is in screw-thread fit with the spiral sleeve.

A further technical scheme is as follows.

The lifting rod fixed part is provided with a plurality of upright posts. The anti-pinch spring sleeves the upright post. The top of the upright post is provided with a disc.

A further technical scheme is as follows.

The top of the lifting cover plate is connected with a display panel. The lifting cover plate is provided with a display threading pipe. The display threading pipe penetrates through the lifting rod fixed part for a line to pass through and be connected with the display panel.

A further technical scheme is as follows.

The air disinfector also includes installation structures for filter units of the disinfector. The installation structures include filter units, installation units and a bottom cover which are arranged in the shell. The filter units include a filter element, an activated carbon filter screen, a photocatalyst lampshade and a plurality of ultraviolet light tubes which are sequentially sleeved from outside to inside. The filter element is arranged on the bottom cover. The installation units include a light tube fixing clip, a light tube fixed knob and a light tube fixed part. The circumference of the light tube fixing clip is provided with a plurality of spring pieces. A locating space is formed among the spring pieces. The number of the ultraviolet light tubes is multiple. The tops of the ultraviolet light tubes are located in the locating space. The light tube fixing clip is located on the top inside the photocatalyst lampshade. The bottom of the photocatalyst lampshade is provided with a limit ring. The light tube fixed knob sleeves the limit ring. A locating slot is formed in the limit ring. The light tube fixed part is provided with a located block matched with the locating slot. The light tube fixed knob is in screw-thread fit with the light tube fixed part. The light tube fixed part is arranged on the bottom cover.

A further technical scheme is as follows.

The bottom of the lamp tube fixed part is fixedly connected with a contact chip fixed part. The contact chip fixed part is installed on the bottom cover through threads. The inner bottom of the shell is provided with spring contacts.

The contact chip fixed part is provided with lamp holder contact pins and contact contact pieces sequentially from top to bottom. The top of the lamp holder contact pin is in contact with the bottom of the ultraviolet light tube. The bottom of the lamp holder contact pin is in contact with the top of the contact contact piece. The bottom of the contact contact piece is in contact with the spring contacts. The spring contacts are used for being in circuit connection with a ballast. The ballast is in circuit connection with a master controller.

A further technical scheme is as follows.

The bottom of the bottom cover is provided with a guide plate. A guide slot matched with the guide plate is formed in the inner bottom of the shell. The guide slot is internally and rotatably provided with a plurality of rollers.

A slot is formed in the inner bottom of the shell. The bottom cover is provided with a locating mechanism. The locating mechanism includes an inserted plate and reset springs. The inserted plate is vertically and slidably arranged on the bottom cover. Both ends of the reset spring act on the bottom cover and the inserted plate respectively to provide force for the inserted plate to enter the slot.

A further technical scheme is as follows.

An opening is formed in the back of the shell. Two locking slots are symmetrically formed in the bottom of the opening. The top of the opening is provided with a first magnetic attraction part and also includes a cover plate. The top of the cover plate is provided with a second magnetic attraction part. The bottom of the cover plate is provided with locating plates matched with the locking slots. The first magnetic attraction part and the second magnetic attraction part are magnetically attracted.

The present disclosure has the following working principles and beneficial effects. When the air outlet window works normally, a power source arranged in the air outlet window drives the lifting rod fixed part to rise. The air guide cover is placed on the lifting rod fixed part to push the air guide cover to rise and adjust the gap between the air guide cover and the air outlet window. When the air guide cover rises to the position of the lifting cover plate, the air guide cover does not rise any more. When the disinfector is turned off, the air guide cover needs to be buckled to an upper opening of the air outlet window. At this time, the power source drives the lifting rod fixed part to descend. At this time, if someone accidentally puts his finger into the gap between the air guide cover and the air outlet window, the air guide cover can be blocked from continuing to descend after touching his finger, and the anti-pinch spring converts extrusion force into flexible elastic force to prevent from causing injury to human bodies. The anti-pinch limit switch is in a spring piece type, and the anti-pinch trigger part is located at the bottom of the air guide cover. Under normal conditions, the anti-pinch trigger part and the spring sheet of the anti-pinch limit switch always keep in contact with each other. The anti-pinch limit switch is always pressed by the anti-pinch trigger part. The finger blocks the air guide cover from continuing to descend, but the lifting rod fixed part can continue to descend, so that the anti-pinch trigger part is out of contact with spring pieces of the anti-pinch limit switch. The finger can be taken out when a signal is transmitted to the power source to stop running, thus avoiding the problem that the gap between the air guide cover and the air outlet window hurts hands. The disinfector can be turned off immediately after being caught by hands, and the force is converted into the flexible elastic force after the hands are extruded without causing injury to human bodies.

BRIEF DESCRIPTION OF THE DRAWINGS

The present disclosure is further described in detail in conjunction with the following attached figures and specific embodiments.

Figure 1:
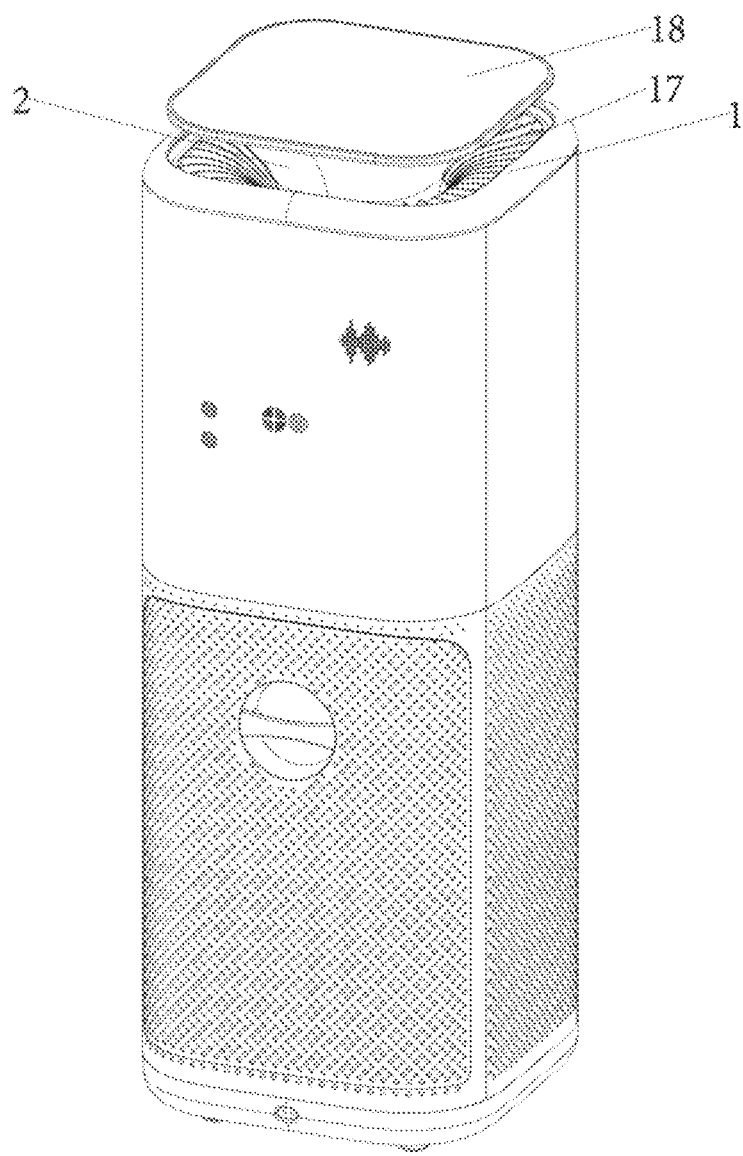
FIG. 1 is an outline schematic diagram of a disinfector main body in the present disclosure.
Figure 2:
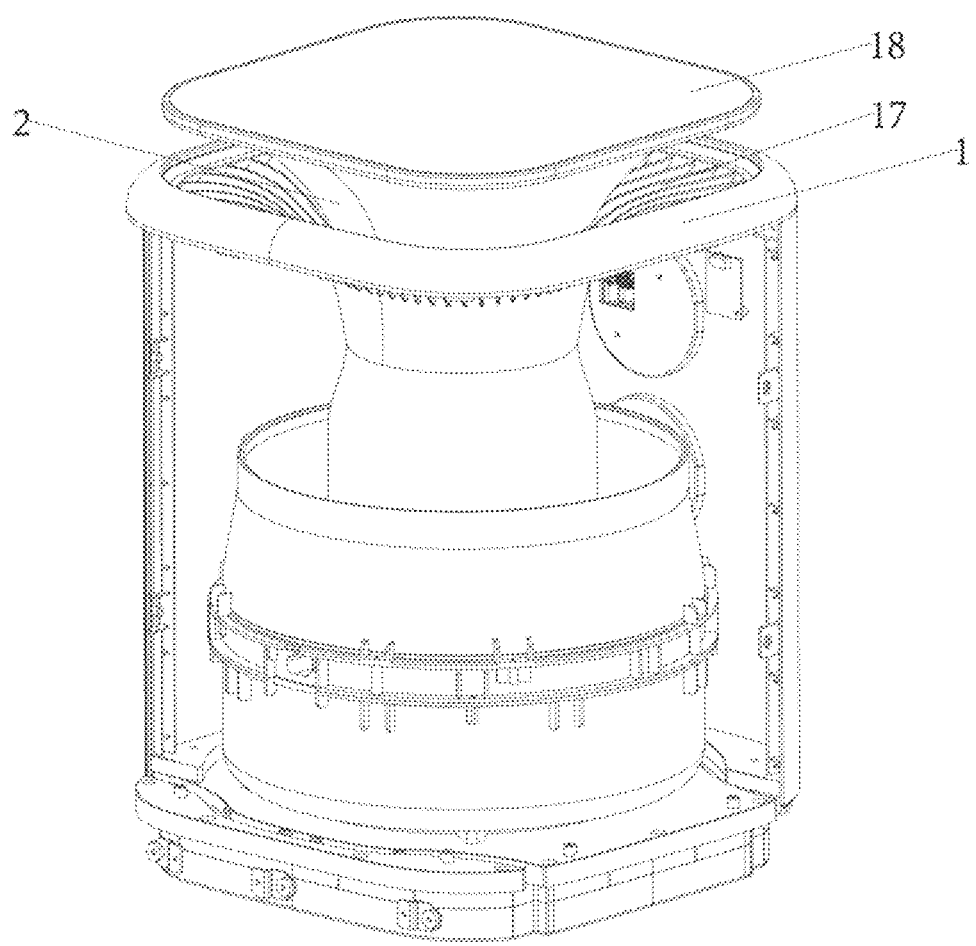
FIG. 2 is a structural schematic diagram inside a shell of a disinfector in the present disclosure.
Figure 3:
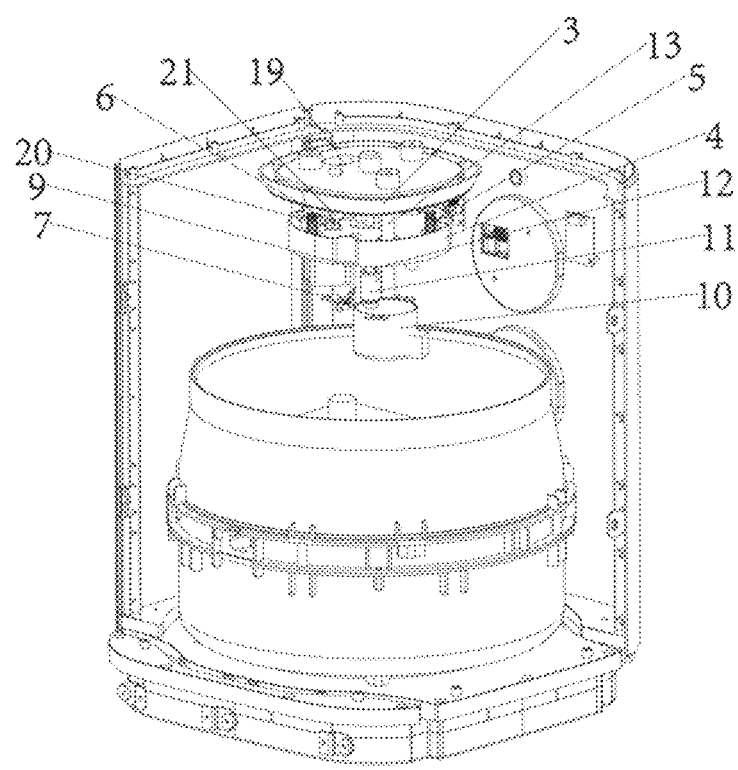
FIG. 3 is a schematic diagram of installation structures such as a lifting structure inside a disinfector in the present disclosure.
Figure 4:
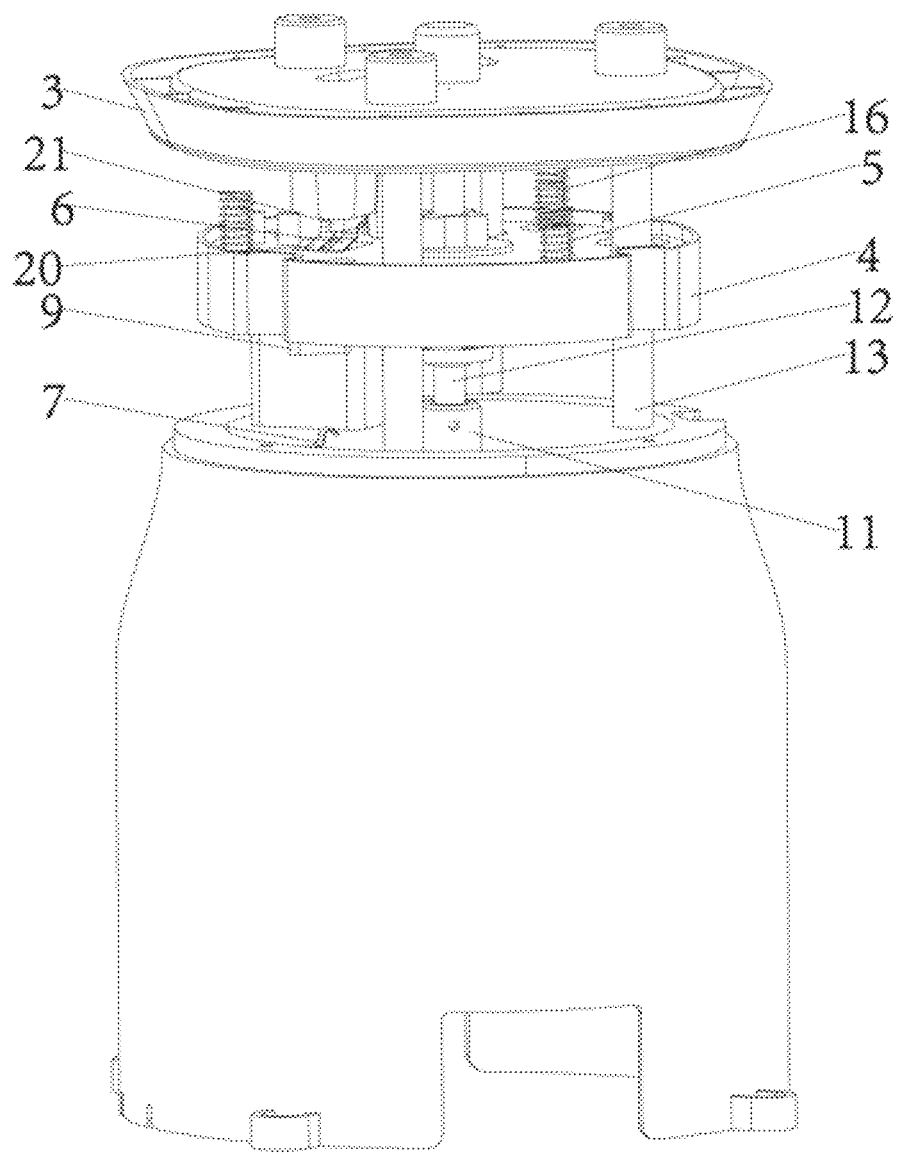
FIG. 4 is an isometric view of a lifting structure at one angle in the present disclosure.
Figure 5:
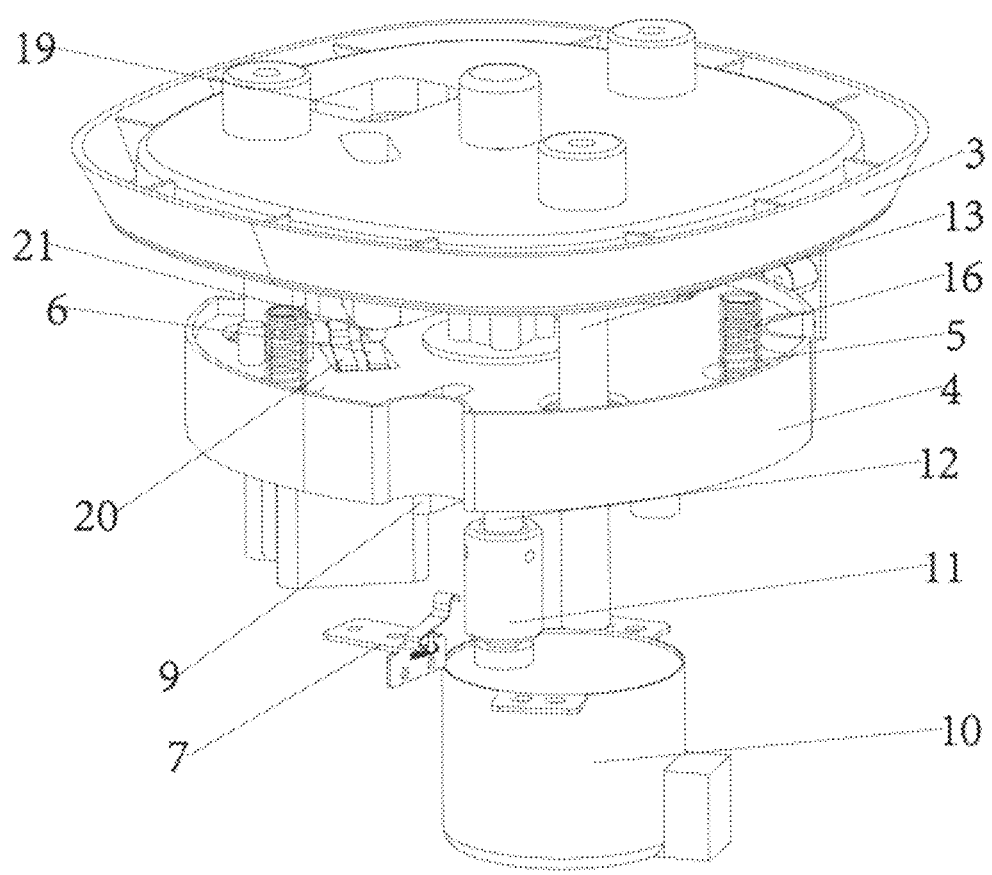
FIG. 5 is an isometric view of a lifting structure at another angle in the present disclosure.
Figure 6:
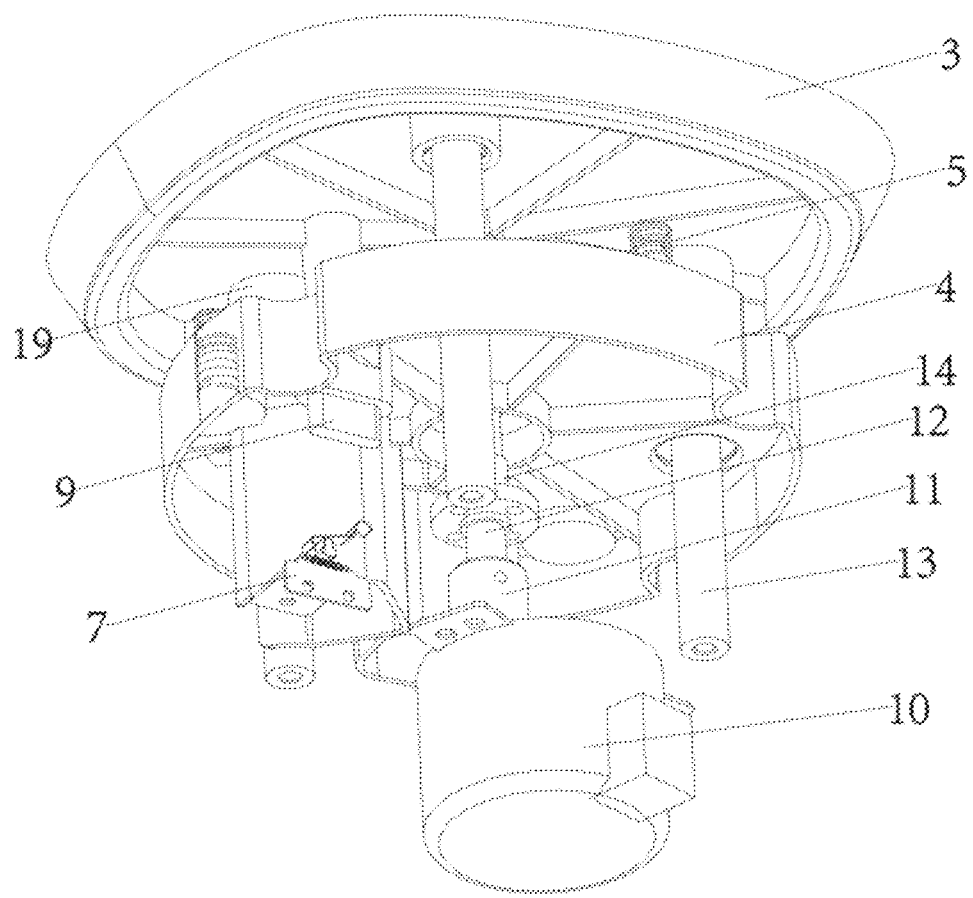
FIG. 6 is a structural schematic diagram at the bottom of a lifting structure in the present disclosure.

Reference signs: 1, air outlet window; 2, air guide cover; 3, lifting cover plate; 4, lifting rod fixed part; 5, anti-pinch spring; 6, top limit switch; 7, bottom limit switch; 8, anti-pinch trigger part; 9, lower trigger part; 10, lifting motor; 11, screw fixed part; 12, lifting screw; 13, lifting limit rod; 14, spiral sleeve; 15, accommodating slot; 16, upright post; 17, shell; 18, display panel; 19, display threading pipe; 20, anti-pinch limit switch; 21, upper trigger part; 22, bottom cover; 23, filter element; 24, activated carbon filter screen; 25, photocatalyst lampshade; 26, ultraviolet light tube; 27, light tube fixing clip; 28, light tube fixed knob; 29, light tube fixed part; 30, spring piece; 31, locating space; 32, limit ring; 33, locating slot; 34, located block; 35, contact chip fixed part; 36, spring contact; 37, lamp holder contact pin; 38, contact contact piece; 39, ballast; 40, guide plate; 41, guide slot; 42, roller; 43, slot; 44, inserted plate; 45, reset spring;

46, locking slot; 47, first magnetic attraction part; 48, cover plate; 49, second magnetic attraction part; and 50, locating plate.

DETAILED DESCRIPTION OF THE EMBODIMENTS

The following clearly and completely describes the technical scheme in the embodiments of the present disclosure with reference to the embodiments of the present disclosure. Apparently, the described embodiments are merely a part rather than all of the embodiments of the present disclosure. Based on the embodiment in the present disclosure, all other embodiments obtained by the ordinary technical staff in the art under the premise of without contributing creative labor relate to the scope protected by the present disclosure.

As shown in FIG. 1 to FIG. 17, the embodiment provides an air disinfector. The air disinfector includes a shell 17, an air outlet window 1 arranged in the shell 17, and an air guide cover 2 vertically and slidably arranged in the air outlet window 1 by means of a lifting mechanism. The lifting mechanism includes a lifting cover plate 3, a lifting rod fixed part 4, a plurality of anti-pinch springs 5 and an anti-pinch limit switch 20. The lifting cover plate 3 is arranged in the air outlet window 1. The lifting rod fixed part 4 is vertically and slidably arranged in the air outlet window 1. The number of the anti-pinch springs 5 is multiple. Both ends of the anti-pinch spring 5 act on the lifting rod fixed part 4 and the air guide cover 2 respectively. The anti-pinch limit switch 20 is arranged on the lifting rod fixed part 4. The air guide cover 2 is placed on the top of the lifting rod fixed part 4. The bottom of the air guide cover 2 is provided with an anti-pinch trigger part 8. The anti-pinch trigger part 8 is in contact with the anti-pinch limit switch 20.

In the embodiment, when the air outlet window 1 works normally, a power source arranged in the air outlet window 1 drives the lifting rod fixed part 4 to rise. The air guide cover 2 is placed on the lifting rod fixed part 4 to push the air guide cover 2 to rise and adjust the gap between the air guide cover 2 and the air outlet window 1. When the air guide cover 2 rises to the position of the lifting cover plate 3, the air guide cover 2 does not rise any more. When the disinfector is turned off, the air guide cover 2 needs to be buckled to an upper opening of the air outlet window 1. At this time, the power source drives the lifting rod fixed part 4 to descend. At this time, if someone accidentally puts his finger into the gap between the air guide cover 2 and the air outlet window 1, the air guide cover 2 can be blocked from continuing to descend after touching his finger, and the anti-pinch spring 5 converts extrusion force into flexible elastic force to prevent from causing injury to human bodies. The anti-pinch limit switch 20 is in a spring piece type, and the anti-pinch trigger part 8 is located at the bottom of the air guide cover 2. Under normal conditions, the anti-pinch trigger part 8 and the spring sheet of the anti-pinch limit switch 20 always keep in contact with each other. The anti-pinch limit switch 20 is always pressed by the anti-pinch trigger part 8. The finger blocks the air guide cover 2 from continuing to descend, but the lifting rod fixed part 4 can continue to descend, so that the anti-pinch trigger part 8 is out of contact with spring pieces of the anti-pinch limit switch 20. The finger can be taken out when a signal is transmitted to the power source to stop running, thus avoiding the problem that the gap between the air guide cover 2 and the air outlet window 1 hurts hands. The disinfector can be turned off immediately after being caught by hands, and the force is converted into the flexible elastic force after the hands are extruded without causing injury to human bodies.

Further, the air disinfector also includes the followings.

The lifting rod fixed part 4 is provided with a top limit switch 6. The lifting cover plate 3 is provided with an upper trigger part 21 corresponding to the top limit switch 6. An inner wall of the air outlet window 1 is provided with a bottom limit switch 7. The bottom of the lifting rod fixed part 4 is provided with a lower trigger part 9 corresponding to the bottom limit switch 7.

Figure 7:
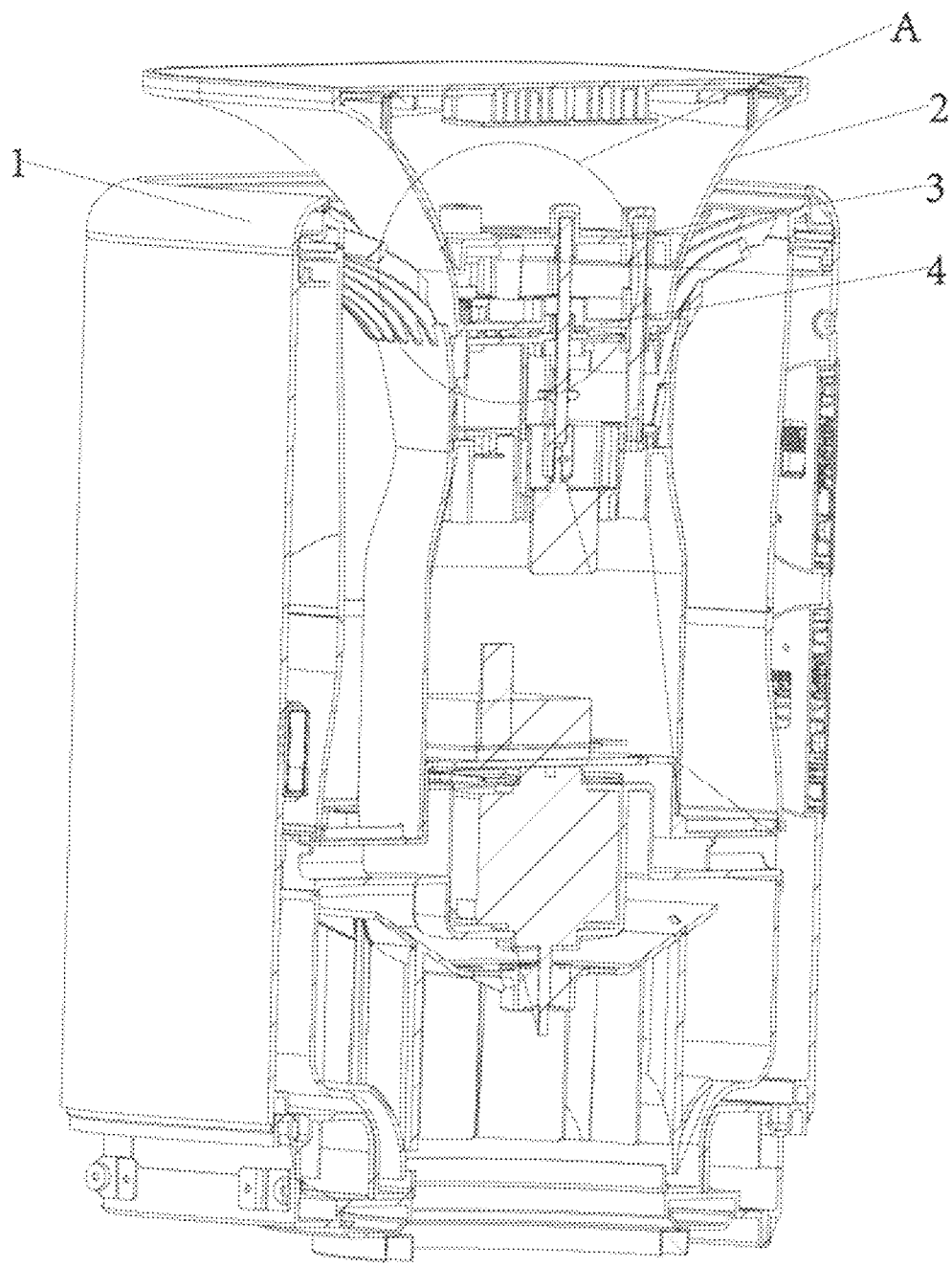
FIG. 7 is a section view of an internal structure of a disinfector in the present disclosure.
Figure 8:
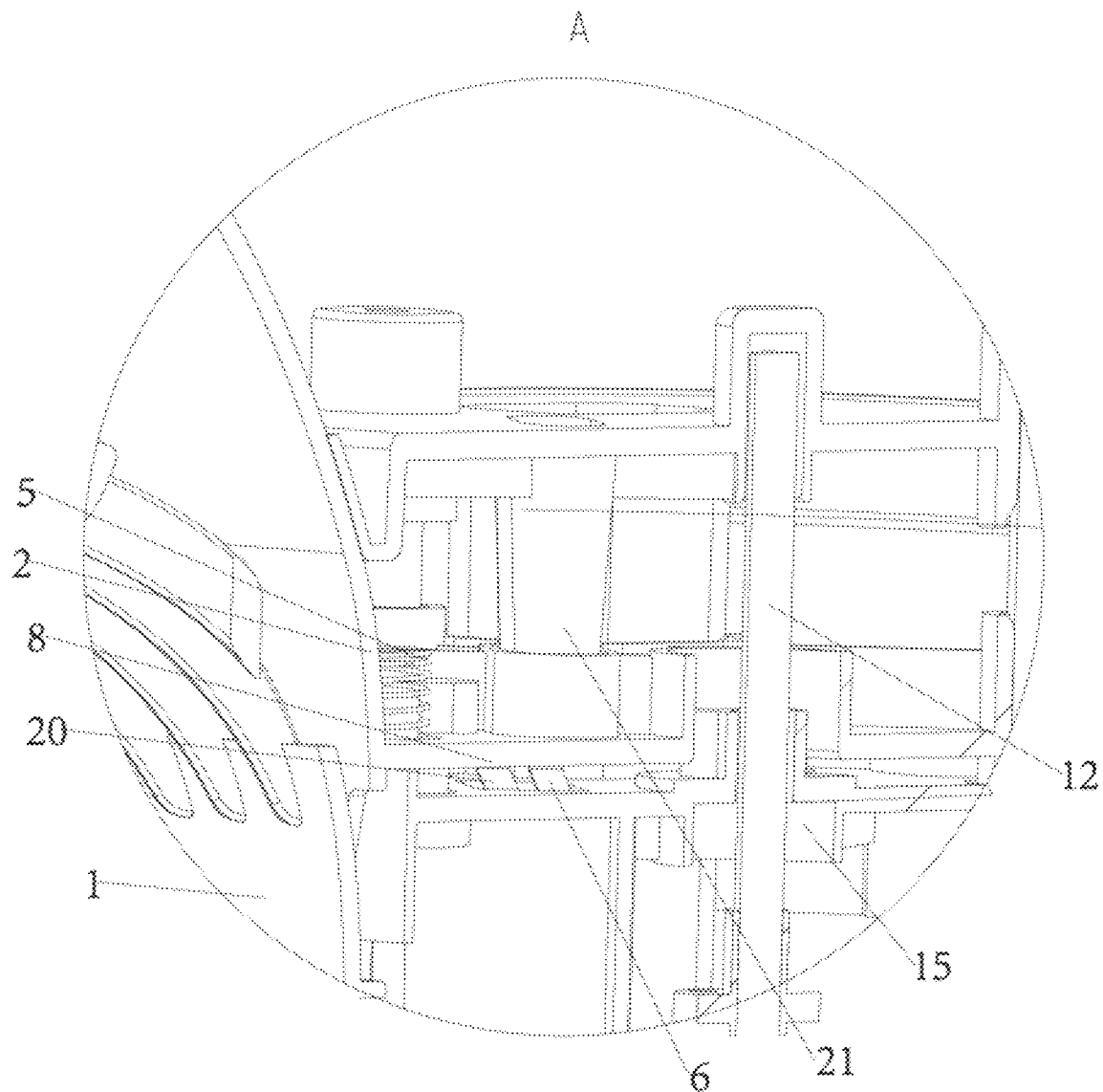
FIG. 8 is an enlarged view of part A in FIG. 7 in the present disclosure.
Figure 9:
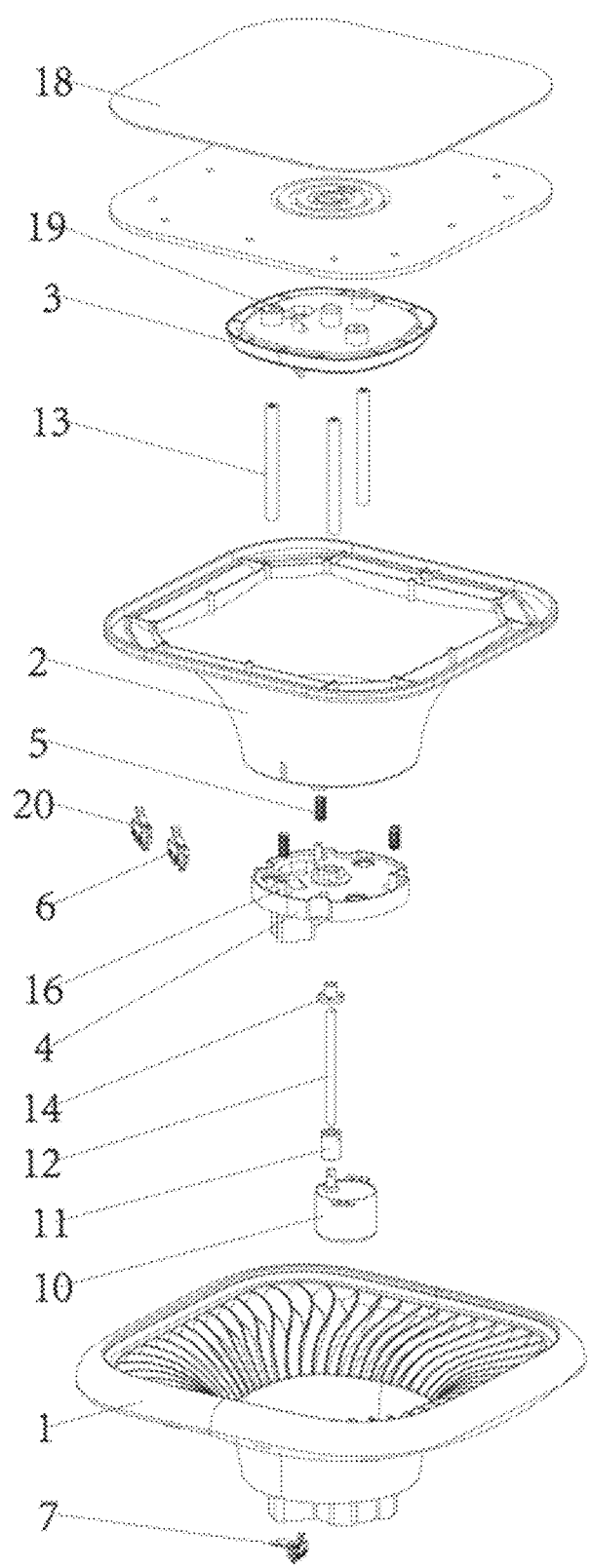
FIG. 9 is an explosive view of a lifting structure in the present disclosure.

In the embodiment, when the air outlet window 1 works normally, the power source arranged in the air outlet window 1 drives the lifting rod fixed part 4 to rise to push the air guide cover 2 to rise and adjust the gap between the air guide cover 2 and the air outlet window 1. The lifting cover plate 3 is fixedly installed in the air outlet window 1. When the air guide cover 2 rises to the position of the lifting cover plate 3, the top limit switch 6 is in contact with the upper trigger part 21 at the bottom of the lifting cover plate 3 to trigger the top limit switch 6 and transmit a signal to the power source to stop running. When the disinfector is turned off, the air guide cover 2 descends in the air outlet window 1. When the air guide cover 2 descends so that the bottom limit switch 7 installed in the air outlet window 1 is in contact with the lower trigger part 9 at the bottom of the lifting rod fixed part 4, the bottom limit switch 7 is triggered to transmit a signal to the power source to stop running. The power source is intelligently and automatically turned on and off, and the air guide cover 2 is automatically lifted. FIG. 7 and FIG. 8 illustrate the structures of the upper trigger part 21 at the bottom of the air guide cover and the top limit switch 6.

Further, the air disinfector also includes the followings.

The air outlet window 1 is provided with a lifting motor 10. An output shaft of the lifting motor 10 is connected with a lifting screw 12 by means of a screw fixed part 11. The lifting screw 12 is in screw-thread fit with the lifting rod fixed part 4. The top of the lifting screw 12 abuts against the bottom of the lifting cover plate 3.

The air disinfector also includes a plurality of lifting limit rods 13. The lifting limit rods 13 are arranged on the lifting cover plate 3. The lifting limit rods 13 penetrate through the lifting rod fixed part 4.

In the embodiment, the power source is a lifting motor 10. The lifting motor 10 is fixedly arranged in the air outlet window. An output shaft of the lifting motor 10 is connected with a lifting screw 12 by means of a screw fixed part 11. The lifting screw 12 is in screw-thread fit with the lifting rod fixed part 4, so that the lifting of the lifting rod fixed part 4 is controlled. The top of the lifting screw 12 abuts against the bottom of the lifting cover plate 3. During rising, the top of the lifting screw 12 rotates relatively to the lifting cover plate 3. The lifting limit rod 13 plays a guiding role. At the same time, radial movement between the lifting cover plate 3 and the lifting rod fixed part 4 is limited, so that normal lifting is ensured.

Further, the air disinfector also includes the followings.

An accommodating slot 15 is formed in the center of the lifting rod fixed part 4. A spiral sleeve 14 is installed in the accommodating slot 15. The lifting screw 12 is in screw-thread fit with the spiral sleeve 14.

Further, the air disinfector also includes the followings.

The lifting rod fixed part 4 is provided with a plurality of upright posts 16. The anti-pinch spring 5 sleeves the upright post 16. The top of the upright post 16 is provided with a disc.

Further, the air disinfector also includes the followings.

The top of the lifting cover plate 3 is connected with a display panel 18. The lifting cover plate 3 is provided with a display threading pipe 19. The display threading pipe 19 penetrates through the lifting rod fixed part 4 for a line to pass through and be connected with the display panel 18.

Figure 10:
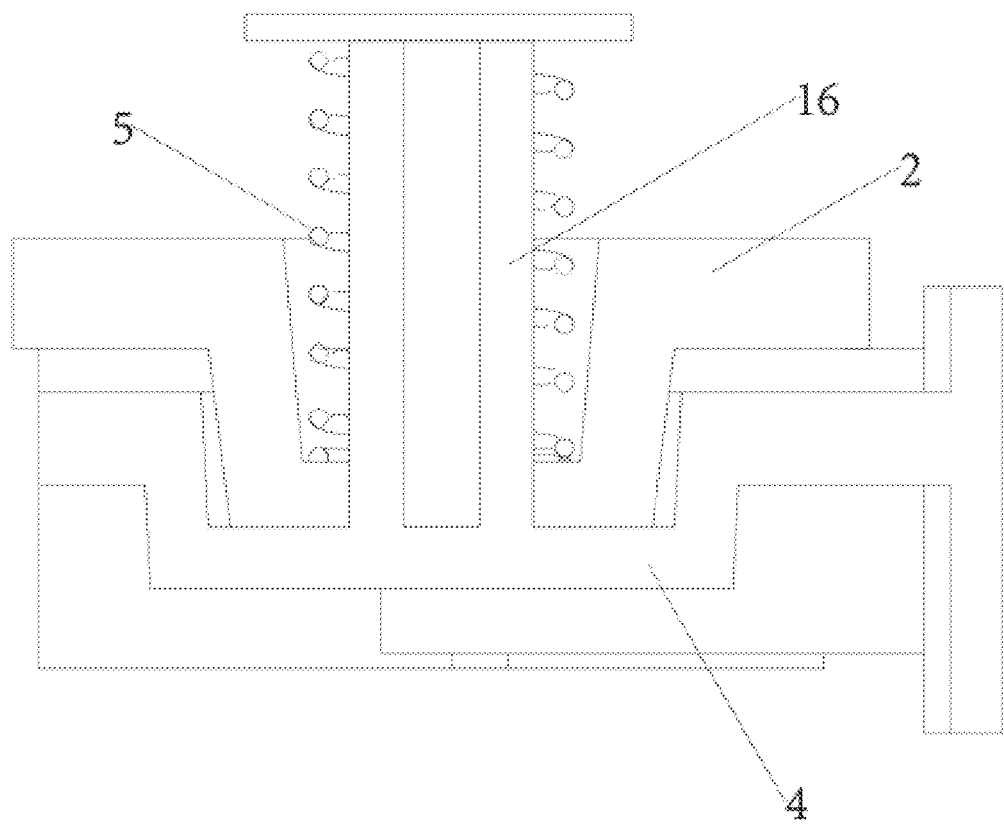
FIG. 10 is an installation schematic diagram of an anti-pinch spring in the present disclosure.
Figure 11:
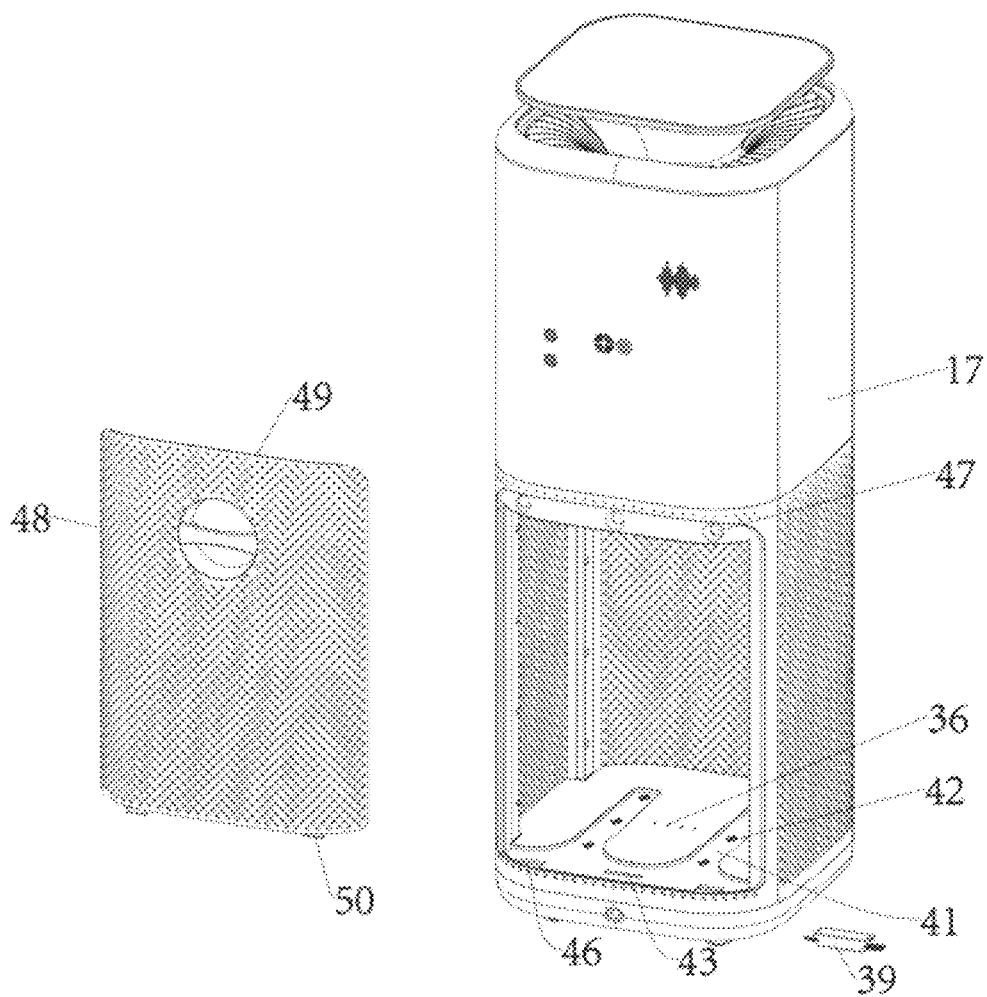
FIG. 11 is an outline schematic diagram of a shell in the present disclosure.
Figure 12:
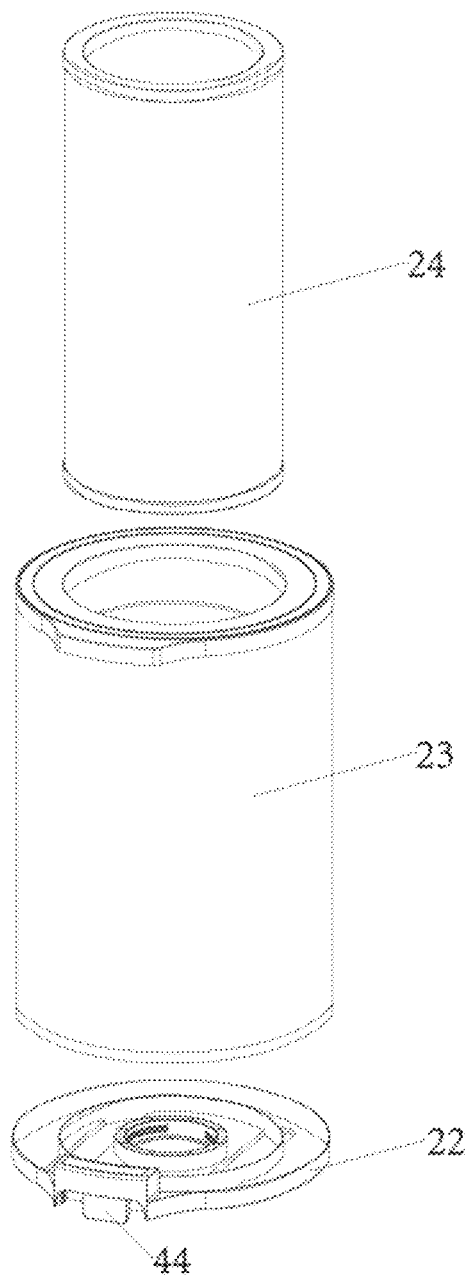
FIG. 12 is an explosive view of installation structures such as a filter element and an activated carbon filter screen in the present disclosure.
Figure 13:
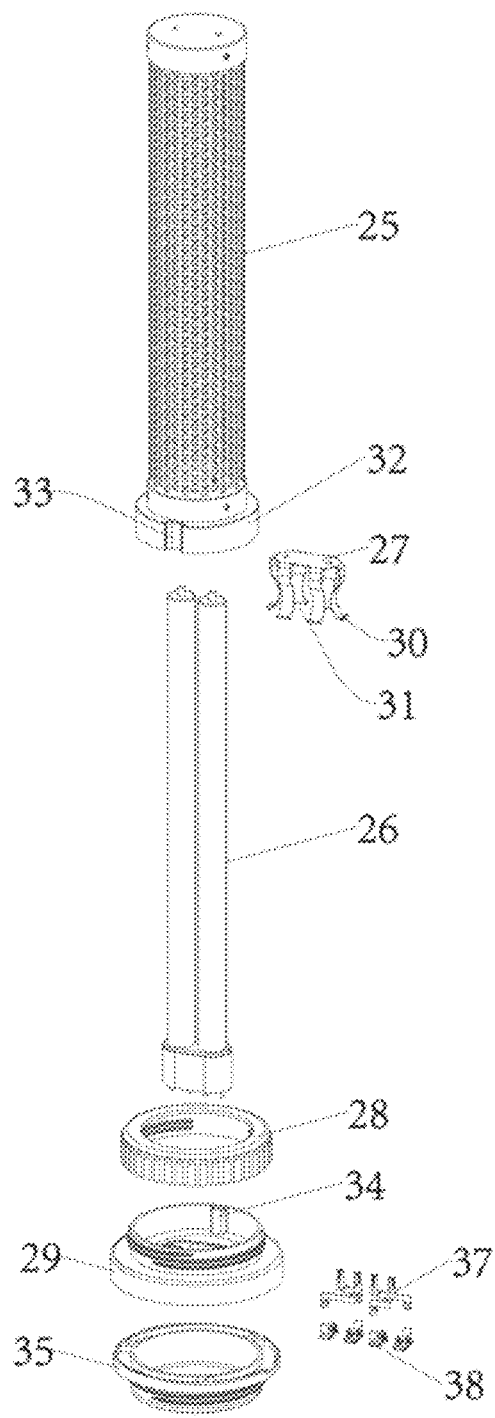
FIG. 13 is an explosive view of installation structures such as ultraviolet light tubes in the present disclosure.
Figure 14:
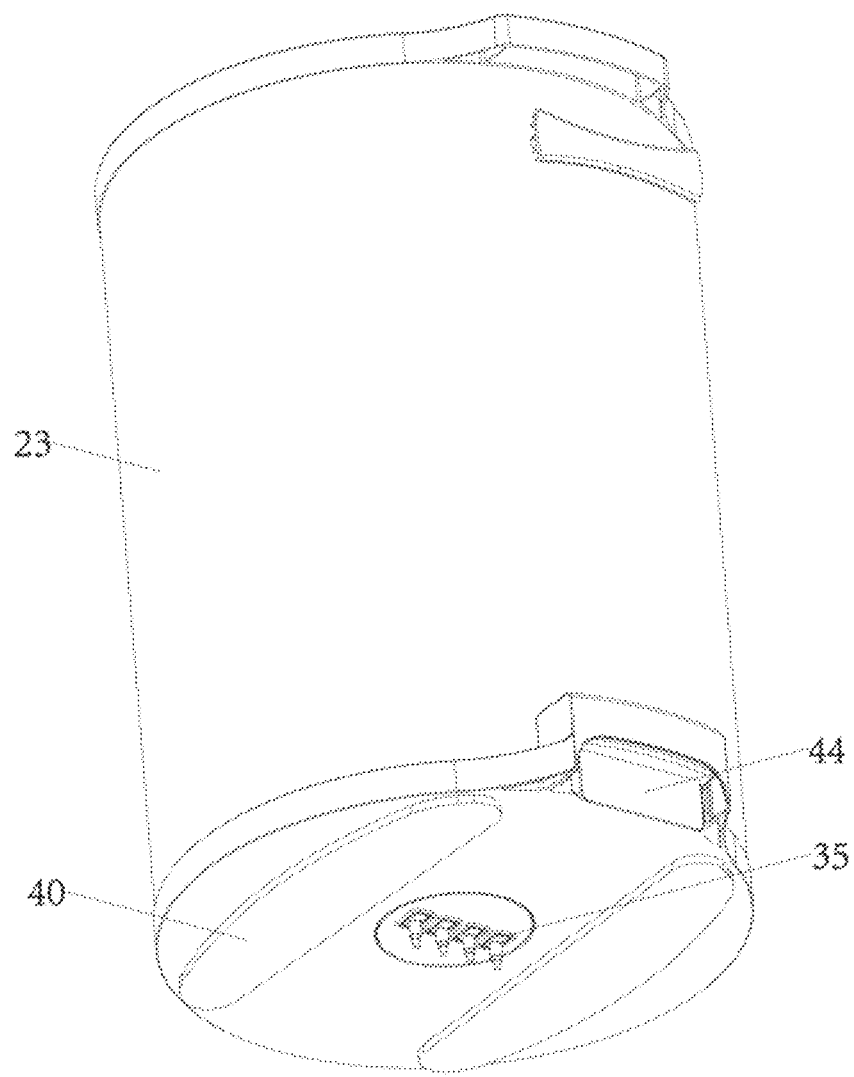
FIG. 14 is a structural schematic diagram at the bottom of a filter element in the present disclosure.
Figure 15:
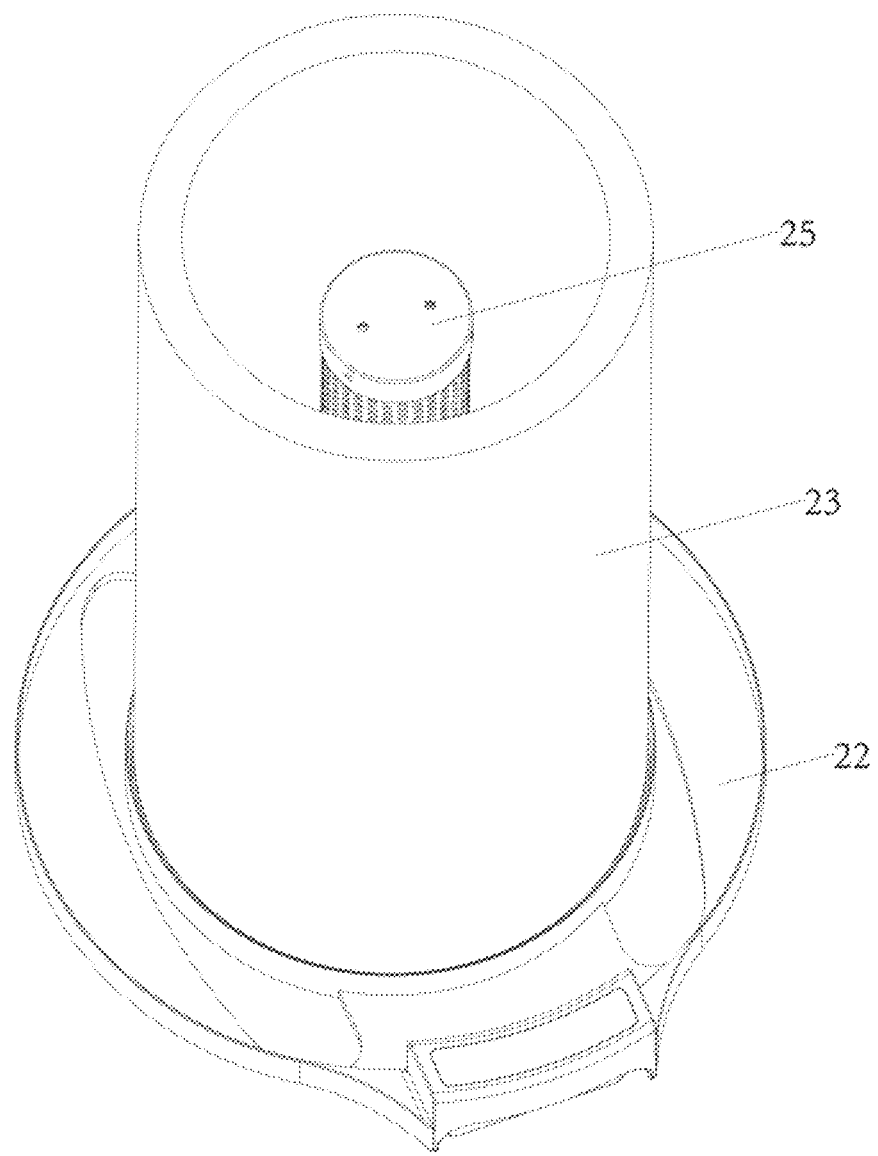
FIG. 15 is an installation state schematic diagram of a filter element in the present disclosure.
Figure 16:
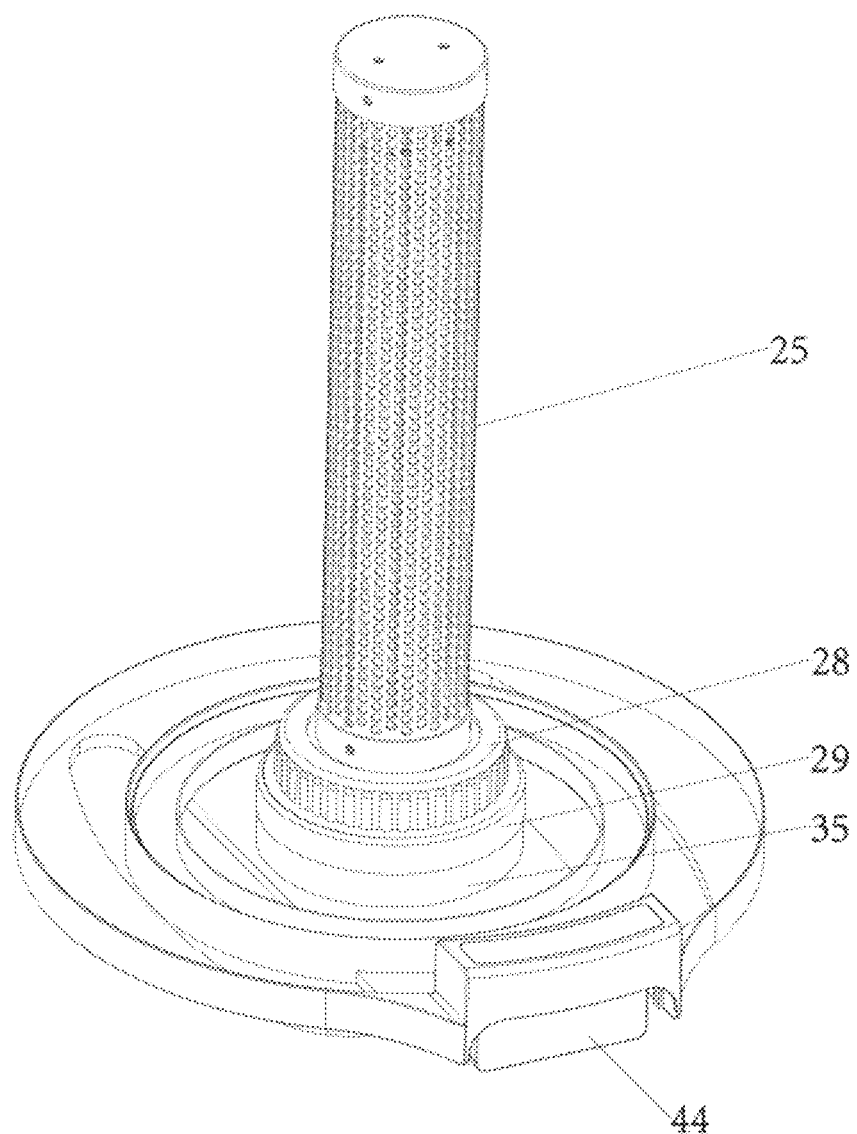
FIG. 16 is an installation state schematic diagram of a photocatalyst lampshade in the present disclosure.
Figure 17:
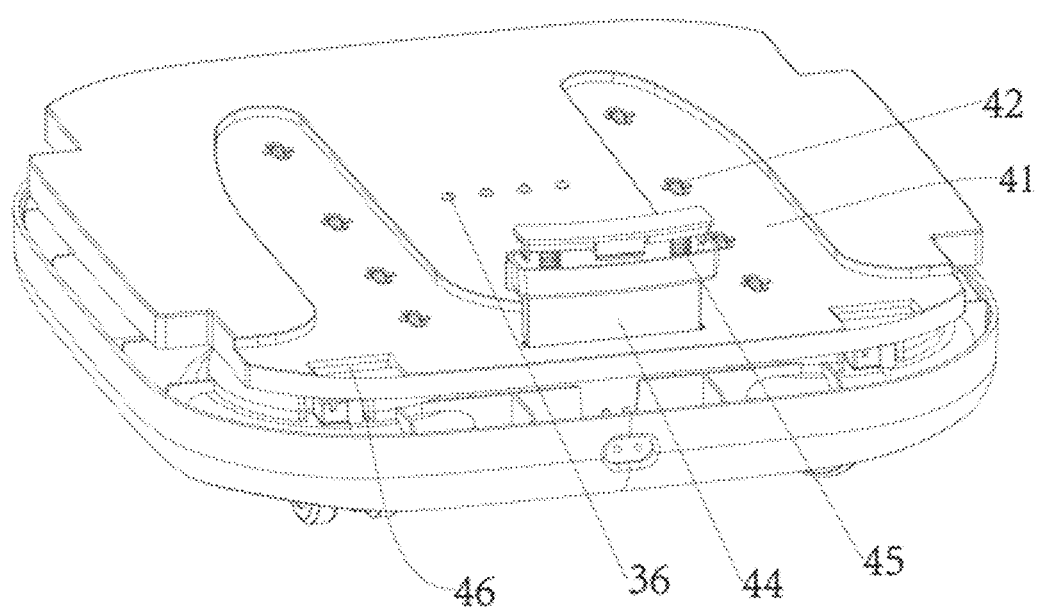
FIG. 17 is a structural schematic diagram at the inner bottom of a shell in the present disclosure.

In the embodiment, the upright post 16 plays a guiding role to ensure that the anti-pinch spring 5 is not offset in the axial direction. The top of the upright post 16 is provided with a disc. Due to the fact that the internal structure is relatively complicated, the disc is not embodied in FIG. 1 to FIG. 9. The relationship among the anti-pinch spring 5, the upright post 16 and the air guide cover 2 is shown in FIG. 10. The upright post 16 is arranged on the lifting rod fixed part 4. The anti-pinch spring 5 sleeves the upright post 16. Both ends of the anti-pinch spring 5 act on the disc and the air guide cover 2 respectively. The circumference of the air outlet window 1 is provided with a plurality of flow deflectors. Through the flow deflectors, the air in the disinfector eddies and is dispersed more uniformly. A through hole is formed in the lifting rod fixed part 4. The display threading pipe 19 is located in the through hole. The display threading pipe 19 is used for a line to pass through and be in line connection with a master controller and the display panel 18, so that the display panel 18 can display the running condition of the disinfector visually.

Further, the air disinfector also includes the followings.

The air disinfector also includes installation structures for filter units of the disinfector. The installation structures include filter units, installation units and a bottom cover 22 which are arranged in the shell 17. The filter units include a filter element 23, an activated carbon filter screen 24, a photocatalyst lampshade 25 and a plurality of ultraviolet light tubes 26 which are sequentially sleeved from outside to inside. The filter element 23 is arranged on the bottom cover 22. The installation units include a light tube fixing clip 27, a light tube fixed knob 28 and a light tube fixed part 29. The circumference of the light tube fixing clip 27 is provided with a plurality of spring pieces 30. A locating space 31 is formed among the spring pieces 30. The number of the ultraviolet light tubes 26 is multiple. The tops of the ultraviolet light tubes 26 are located in the locating space 31. The light tube fixing clip 27 is located on the top inside the photocatalyst lampshade 25. The bottom of the photocatalyst lampshade 25 is provided with a limit ring 32. The light tube fixed knob 28 sleeves the limit ring 32. A locating slot 33 is formed in the limit ring 32. The light tube fixed part 29 is provided with a located block 34 matched with the locating slot 33. The light tube fixed knob 28 is in screw-thread fit with the light tube fixed part 29. The light tube fixed part 29 is arranged on the bottom cover 22.

In the embodiment, a universal wheel is installed at four corners of the bottom of the shell 17 respectively. The shell 17 is internally provided with a space for accommodating and installing the filter units. The filter units include filter element 23, an activated carbon filter screen 24, a photocatalyst lampshade 25 and a plurality of ultraviolet light tubes 26 which are sequentially sleeved from outside to inside. After air is inhaled, the air passes through the activated carbon filter screen 24, and the air is disinfected under the irradiation of the photocatalyst lampshade 25 by the ultraviolet light tubes 26 and the filtering effect of the activated carbon filter screen 24, and then the air is discharged from an outlet of the disinfector. The bottom cover 22 is installed inside the space of the shell 17. The filter element 23 is installed on the bottom cover 22. The ultraviolet light tubes 26 are installed by means of the installation units. Specifically, the installation units include a light tube fixing clip 27, a light tube fixed knob 28 and a light tube fixed part 29. The light tube fixing clip 27 includes a base plate, and is provided with a plurality of spring pieces 30 in the circumferential direction of the base plate. The spring piece 30 is elastic by means of material characteristics. Ends of the spring piece 30 are expanded outwards, so that the light tubes are convenient to insert. The ultraviolet light tubes 26 are in the type of two tubes, and the cross section is shaped like a figure "8". The ends are inserted among the spring pieces 30 to realize the fixation on the tops of the two ultraviolet light tubes 26. The bottom of the ultraviolet light tube 26 is inserted in the light tube fixed part 29. The ultraviolet light tube 26 is located in the photocatalyst lampshade 25. The bottom of the photocatalyst lampshade 25 is provided with a limit ring 32. The light tube fixed knob 28 is annular and sleeves the limit ring 32. The light tube fixed knob 28 is clamped with the limit ring 32. The light tube fixed knob 28 is provided with an internal thread. The light tube fixed part 29 is provided with an external thread. The light tube fixed knob 28 and the light tube fixed part 29 are in screw-thread fit with each other. The light tube fixed part 29 is arranged on the bottom cover 22. When the light tube fixed knob 28 is screwed in downwards, the limit ring 32 is pressed to drive the photocatalyst lampshade 25 and the ultraviolet light tubes 26 to move downwards, so that the installation is firmer and more reliable. The bottom of the ultraviolet light tube 26 is in circuit connection with the master controller inside the light tube fixed part 29 to ensure normal running of the functions of the disinfector. Two locating slots 33 are formed in the limit ring 32. The light tube fixed part 29 is provided with two located blocks 34 matched with the two locating slots 33. After the photocatalyst lampshade 25 is inserted into the light tube fixed part 29, the located blocks 34 are inserted into the locating slots 33 to limit the radial rotation of the photocatalyst lampshade 25, so that when the light tube fixed knob 28 rotates, the ultraviolet light tubes 26 can keep still. The stability and safety of the structure and the reliability of locating fastening are realized. moreover, the installation structures are simple and ingenious and convenient to disassemble and assemble. The filter element 23 is convenient to maintain and replace after the disinfector is opened.

Further, the air disinfector also includes the followings.

The bottom of the lamp tube fixed part 29 is fixedly connected with a contact chip fixed part 35. The contact chip fixed part 35 is installed on the bottom cover 22 through threads. The inner bottom of the shell 17 is provided with spring contacts 36.

The contact chip fixed part 35 is provided with lamp holder contact pins 37 and contact contact pieces 38 sequentially from top to bottom. The top of the lamp holder contact pin 37 is in contact with the bottom of the ultraviolet light tube 26. The bottom of the lamp holder contact pin 37 is in contact with the top of the contact contact piece 38. The bottom of the contact contact piece 38 is in contact with the spring contacts 36. The spring contacts 36 are used for being in circuit connection with a ballast 39. The ballast 39 is in circuit connection with a master controller.

In the embodiment, the bottom of the light tube fixed part 29 is in threaded connection with a contact chip fixed part 35. The contact chip fixed part 35 is provided with an external thread. An installation hole, which is a threaded hole, is formed in the bottom cover 22. The contact chip fixed part 35 is in screw-thread fit with the bottom cover 22.

The contact chip fixed part 35 is provided with lamp holder contact pins 37 sequentially from top to bottom. Bottom contacts of the ultraviolet light tubes 26, the lamp holder contact pins 37 and the contact contact pieces 38 are in contact with the spring contacts 36 on the bottom cover 22 sequentially. The spring contacts 36 are in circuit connection with the ballast 39. The ballast 39 is in circuit connection with the mater controller. After contact, electrification is realized to control the running of the ultraviolet light tubes 26. The ballast 39 is installed inside the shell 17. The bottom of the spring contact 36 is provided with a spring to provide upward force all the time. When the bottom cover 22 is installed, the spring contact 36 is pressed by the contact contact piece 38. After installation in place, the spring contact 36 is popped up to be connected with the contact contact piece 38.

Further, the air disinfector also includes the followings.

The bottom of the bottom cover 22 is provided with a guide plate 40. A guide slot 41 matched with the guide plate 40 is formed in the inner bottom of the shell 17. The guide slot 41 is internally and rotatably provided with a plurality of rollers 42.

A slot 43 is formed in the inner bottom of the shell 17. The bottom cover 22 is provided with a locating mechanism. The locating mechanism includes an inserted plate 44 and reset springs 45. The inserted plate 44 is vertically and slidably arranged on the bottom cover 22. Both ends of the reset spring 45 act on the bottom cover 22 and the inserted plate 44 respectively to provide force for the inserted plate 44 to enter the slot 43.

Further, the air disinfector also includes the followings.

An opening is formed in the back of the shell 17. Two locking slots 46 are symmetrically formed in the bottom of the opening. The top of the opening is provided with a first magnetic attraction part 47 and also includes a cover plate 48. The top of the cover plate 48 is provided with a second magnetic attraction part 49. The bottom of the cover plate 48 is provided with locating plates 50 matched with the locking slots 46. The first magnetic attraction part 47 and the second magnetic attraction part 49 are magnetically attracted.

In the embodiment, the guide plate 40 is matched with the guide slot 41 to play a guiding role, so that the bottom cover 22 is conveniently inserted into the opening in the back of the shell 17. When the guide plate 40 is inserted, the guide plate 40 is in contact with the rollers 42 inside the guide slot 41. When the rollers 42 roll, the installation is more convenient to avoid sliding friction. The shell 17 is used for accommodating the space of the filter units, the slot 43 is formed in the bottom of the shell 17. When the bottom cover 22 slides in place inwards, the inserted plate 44 corresponds to the slot 43 in position, and is inserted into the slot 43 under the action of the reset springs 45 to realize locating. During disassembling, only the inserted plate 44 needs to be pulled up, and the reset springs 45 are compressed, so that the inserted plate 44 is separated from the slot 43, and a base plate can slip off conveniently and quickly. The bottom of the cover plate 48 is symmetrically provided with a pair of locating plates 50 corresponding to the locking slots 46 in the bottom of the opening. The top of the cover plate 48 is provided with the second magnetic attraction part 49 corresponding to the first magnetic attraction part 47 on the top of the opening. During installation, first the locating plates 50 are inserted into the locking slots 46, and then the top of the opening is covered with the top of the cover plate 48. The first magnetic attraction part 47 and the second magnetic attraction part 49 are magnetically attracted to realize installation and locating.

The foregoing descriptions are merely exemplary embodiments of the present disclosure, but are not intended to limit the present disclosure. Any modification, equivalent replacement, or improvement made within the spirit and principle of the present disclosure shall fall within the protection scope of the present disclosure.

What is claimed is:

1. An air disinfector, comprising a shell (17), an air outlet window (1) arranged in the shell (17), an air guide cover (2) vertically and slidably arranged in the air outlet window (1) by means of a lifting mechanism, and installation structures, wherein the lifting mechanism comprises a lifting cover plate (3), a lifting rod fixed part (4), a plurality of anti-pinch springs (5) and an anti-pinch limit switch (20), the lifting cover plate (3) is arranged in the air outlet window (1), the lifting rod fixed part (4) is vertically and slidably arranged in the air outlet window (1), the number of the anti-pinch springs (5) is multiple, both ends of the anti-pinch spring (5) act on the lifting rod fixed part (4) and the air guide cover (2) respectively, the anti-pinch limit switch (20) is arranged on the lifting rod fixed part (4), the air guide cover (2) is placed on a top of the lifting rod fixed part (4), a bottom of the air guide cover (2) is provided with an anti-pinch trigger part (8), and the anti-pinch trigger part (8) is in contact with the anti-pinch limit switch (20); the air guide cover (2) stops descending after being in contact with fingers, elastic extrusion force is generated by means of deformation of the anti-pinch spring (5), and the anti-pinch trigger part (8) is out of contact with the anti-pinch limit switch (20) to send a stop signal;

the installation structures comprise filter units, installation units and a bottom cover (22) which are arranged in the shell (17), the filter units comprise a filter element (23), an activated carbon filter screen (24), a photocatalyst lampshade (25) and a plurality of ultraviolet light tubes (26) which are sequentially sleeved from outside to inside, the filter element (23) is arranged on the bottom cover (22), the installation units comprise a light tube fixing clip (27), a light tube fixed knob (28) and a light tube fixed part (29), a circumference of the light tube fixing clip (27) is provided with a plurality of spring pieces (30), a locating space (31) is formed among the spring pieces (30), the number of the ultraviolet light tubes (26) is multiple, tops of the ultraviolet light tubes (26) are located in the locating space (31), the light tube fixing clip (27) is located on a top inside the photocatalyst lampshade (25), a bottom of the photocatalyst lampshade (25) is provided with a limit ring (32), the light tube fixed knob (28) sleeves the limit ring (32), a locating slot (33) is formed in the limit ring (32), the light tube fixed part (29) is provided with a located block (34) matched with the locating slot (33), the light tube fixed knob (28) is in screw-thread fit with the light tube fixed part (29), and the light tube fixed part (29) is arranged on the bottom cover (22).

2. The air disinfector according to claim 1, wherein the lifting rod fixed part (4) is provided with a top limit switch (6), the lifting cover plate (3) is provided with an upper trigger part (21) corresponding to the top limit switch (6), an inner wall of the air outlet window (1) is provided with a bottom limit switch (7), and a bottom of the lifting rod fixed part (4) is provided with a lower trigger part (9) corresponding to the bottom limit switch (7).

3. The air disinfector according to claim 1, wherein the air outlet window (1) is provided with a lifting motor (10), an output shaft of the lifting motor (10) is connected with a lifting screw (12) by means of a screw fixed part (11), the lifting screw (12) is in screw-thread fit with the lifting rod fixed part (4), and a top of the lifting screw (12) abuts against a bottom of the lifting cover plate (3); and the air disinfector also comprises a plurality of lifting limit rods (13), wherein the lifting limit rods (13) are arranged on the lifting cover plate (3), and the lifting limit rods (13) penetrate through the lifting rod fixed part (4).

4. The air disinfector according to claim 3, wherein an accommodating slot (15) is formed in a center of the lifting rod fixed part (4), a spiral sleeve (14) is installed in the accommodating slot (15), and the lifting screw (12) is in screw-thread fit with the spiral sleeve (14).

5. The air disinfector according to claim 1, wherein the lifting rod fixed part (4) is provided with a plurality of upright posts (16), the anti-pinch spring (5) sleeves the upright post (16), and a top of the upright post (16) is provided with a disc.

6. The air disinfector according to claim 1, wherein a top of the lifting cover plate (3) is connected with a display panel (18), the lifting cover plate (3) is provided with a display threading pipe (19), and the display threading pipe (19) penetrates through the lifting rod fixed part (4) for a line to pass through and be connected with the display panel (18).

7. The air disinfector according to claim 1, wherein a bottom of the lamp tube fixed part (29) is fixedly connected with a contact chip fixed part (35), the contact chip fixed part (35) is installed on the bottom cover (22) through threads, and an inner bottom of the shell (17) is provided with spring contacts (36); and the contact chip fixed part (35) is provided with lamp holder contact pins (37) and contact contact pieces (38) sequentially from top to bottom, a top of the lamp holder contact pin (37) is in contact with a bottom of the ultraviolet light tube (26), a bottom of the lamp holder contact pin (37) is in contact with a top of the contact contact piece (38), a bottom of the contact contact piece (38) is in contact with the spring contacts (36), the spring contacts (36) are used for being in circuit connection with a ballast (39), and the ballast (39) is in circuit connection with a master controller.

8. The air disinfector according to claim 1, wherein a bottom of the bottom cover (22) is provided with a guide plate (40), a guide slot (41) matched with the guide plate (40) is formed in an inner bottom of the shell (17), and the guide slot (41) is internally and rotatably provided with a plurality of rollers (42); and a slot (43) is formed in the inner bottom of the shell (17), the bottom cover (22) is provided with a locating mechanism, the locating mechanism comprises an inserted plate (44) and reset springs (45), the inserted plate (44) is vertically and slidably arranged on the bottom cover (22), both ends of the reset spring (45) act on the bottom cover (22) and the inserted plate (44) respectively to provide force for the inserted plate (44) to enter the slot (43).

9. The air disinfector according to claim 1, wherein an opening is formed in a back of the shell (17), two locking slots (46) are symmetrically formed in a bottom of the opening, a top of the opening is provided with a first magnetic attraction part (47) and also comprises a cover plate (48), a top of the cover plate (48) is provided with a second magnetic attraction part (49), a bottom of the cover plate (48) is provided with locating plates (50) matched with the locking slots (46), and the first magnetic attraction part (47) and the second magnetic attraction part (49) are magnetically attracted.

\* \* \* \* \*